(12) United States Patent
Fung et al.

(10) Patent No.: US 11,722,644 B2
(45) Date of Patent: Aug. 8, 2023

(54) LIVE CATARACT SURGERY VIDEO IN PHACOEMULSIFICATION SURGICAL SYSTEM

(71) Applicant: JOHNSON & JOHNSON SURGICAL VISION, INC., Santa Ana, CA (US)

(72) Inventors: Edith W. Fung, Diamond Bar, CA (US); Katrina T. Lieu, San Diego, CA (US); Jacob S. Childs, Huntington Beach, CA (US); Stephen M. Christopher, Philadelphia, PA (US); Timothy L. Hunter, Corona Del Mar, CA (US); Sandra H. Keh, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 0 days.

(21) Appl. No.: 17/055,597

(22) PCT Filed: Sep. 11, 2019

(86) PCT No.: PCT/IB2019/057654
§ 371 (c)(1),
(2) Date: Nov. 15, 2020

(87) PCT Pub. No.: WO2020/058808
PCT Pub. Date: Mar. 26, 2020

(65) Prior Publication Data
US 2021/0203889 A1 Jul. 1, 2021

Related U.S. Application Data

(60) Provisional application No. 62/733,024, filed on Sep. 18, 2018.

(51) Int. Cl.
*H04N 7/18* (2006.01)
*A61B 34/00* (2016.01)
(Continued)

(52) U.S. Cl.
CPC .............. *H04N 7/183* (2013.01); *A61B 34/25* (2016.02); *A61B 90/37* (2016.02);
(Continued)

(58) Field of Classification Search
CPC ........ H04N 7/183; A61B 90/37; A61B 34/25; G06F 3/0488; G06F 3/0334
(Continued)

(56) References Cited

U.S. PATENT DOCUMENTS

| | | |
|---|---|---|
| 7,400,752 B2 | 7/2008 | Zacharias |
| 8,622,951 B2 | 1/2014 | Claus |

(Continued)

FOREIGN PATENT DOCUMENTS

| | | |
|---|---|---|
| AU | 2015203440 B2 | 1/2017 |
| WO | 9825556 A1 | 6/1998 |
| WO | 0027275 A1 | 5/2000 |

*Primary Examiner* — Thai Q Tran
*Assistant Examiner* — Stephen R Smith
(74) *Attorney, Agent, or Firm* — Johnson & Johnson Surgical Vision, Inc.

(57) ABSTRACT

A Phacoemulsification surgical system provides a live video feed from a camera that is attached to a surgical microscope. The live video feed is shown as part of a graphical user interface (GUI) of phacoemulsification surgical console either in a picture in picture or a full-screen format. The video feed is either static or displayed on-demand as needed during a surgical procedure. The displaying of a live video feed directly on the phacoemulsification surgical console allows for surgical assistants to interact with the live video feed and phacoemulsification surgical system parameters (Continued)

and/or GUI controls without having to refocus on an external object between near and far distances.

26 Claims, 9 Drawing Sheets

(51) Int. Cl.
*A61B 90/00* (2016.01)
*A61F 9/007* (2006.01)
*G06F 3/033* (2013.01)
*G06F 3/0488* (2022.01)

(52) U.S. Cl.
CPC ........ *A61F 9/00745* (2013.01); *G06F 3/0334* (2013.01); *G06F 3/0488* (2013.01)

(58) Field of Classification Search
USPC .................. 348/77; 705/5; 604/22; 382/128
See application file for complete search history.

(56) References Cited

U.S. PATENT DOCUMENTS

| | | |
|---|---|---|
| 9,119,700 B2 | 9/2015 | Boukhny |
| 9,149,340 B2 | 10/2015 | Boukhny et al. |
| 9,171,477 B2 | 10/2015 | Luo et al. |
| 2014/0171959 A1 | 6/2014 | Yacono |
| 2016/0300022 A1* | 10/2016 | Fung .................... A61F 9/00745 |
| 2017/0196453 A1* | 7/2017 | Papac .................. G02B 21/0012 |
| 2018/0333095 A1* | 11/2018 | Sartor ..................... A61B 34/20 |
| 2019/0069957 A1* | 3/2019 | Barral .................... G06N 20/10 |
| 2019/0110855 A1 | 4/2019 | Barral et al. |
| 2020/0015905 A1* | 1/2020 | Scheib .................. A61B 1/018 |
| 2020/0022687 A1* | 1/2020 | Takemoto ............ G06T 7/0012 |
| 2020/0128214 A1* | 4/2020 | Tsuchiya ............ A61B 1/00009 |
| 2020/0129056 A1* | 4/2020 | Soma ....................... A61B 3/10 |
| 2021/0035536 A1* | 2/2021 | Frederick ................ G09G 5/00 |

* cited by examiner

LIVE CATARACT SURGERY VIDEO IN PHACOEMULSIFICATION SURGICAL SYSTEM

CROSS REFERENCE TO RELATED APPLICATIONS

This application is a U.S. national stage of and claims the benefit under 35 U.S.C. § 371 of International Patent Application No. PCT/IB2019/057654, filed Sep. 11, 2019, which claims the benefit under 35 U.S.C. § 119(e) of U.S. Provisional Patent Application No. 62/733,024, filed Sep. 18, 2018, which are incorporated herein by reference in their entirety.

FIELD OF THE INVENTION

The present invention relates to phacoemulsification surgical systems, and, more particularly, a phacoemulsification surgical system comprising a live video feed and graphical user interface.

BACKGROUND OF THE INVENTION

Cataracts affect more than 22 million Americans age 40 and older. And as the U.S. population ages, more than 30 million Americans are expected to have cataracts by the year 2020. Cataract surgery entails the removal of a lens of an eye that has developed clouding of the eye's natural lens, or opacification. As a result of opacification, light is unable to travel to the retina, thereby causing vision loss. Once vision becomes seriously impaired, cataract surgery is a viable option with a high level of success. During cataract surgery, a surgeon replaces the clouded lens with an intraocular lens (IOL).

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

Currently during cataract surgery, a cataract surgeon performs the surgery using a surgical microscope to view a patient's eye. In addition, a camera video recorder is mounted on and connected to the surgical microscope. The camera video recorder may be microscopic camera. This allows for the option to record the surgery by the surgeon, if so desired. Typically, the camera provides video output that can be connected to an external display, such as an external flat screen TV display mounted somewhere in the Operating Room (OR). The display is typically provided for the benefit of those in the OR or nearby, such as other surgeons, scrub techs, nurses, and other staff who may provide assistance to the surgeon so they may see the live video feed of the surgery. Some OR sites do not have an external display, such as a flat screen TV display at all, or even a portion of the setup described above. Live video feeds are considered extremely useful by scrub techs and nurses in assisting with and anticipating a surgeon's needs throughout the cataract surgery procedure. However, live video feed arrangements of the prior art are not considered optimal. Having to reference an external display, such as a flat screen, during a procedure, while useful, is not user friendly. Problems arise when surgical assistants (e.g., scrub techs, nurses) must divert their attention from the patient, surgeon, or phacoemulsification system and focus on the external display. Additionally, surgical assistants are forced to constantly adjust their focus between a phacoemulsification system display screen and an external display screen throughout the surgical procedure.

An external display, such as a separate flat screen TV is typically mounted in the OR to display a live video feed of a surgical procedure. For OR sites that do not even have access to an external display, OR staff are forced to do without a live video feed of a surgical procedure altogether.

BRIEF SUMMARY OF THE INVENTION

The phacoemulsification surgical system adds the capability to take a live video feed from a camera that is attached to a surgical microscope and display the live video feed as part of a graphical user interface (GUI). The live video feed may be a picture in picture or a full-screen format. The video on the phaco surgical system may be static (always on display) or displayed on-demand as needed during surgery. Having the live video feed directly on the phaco surgical system display GUI would allow scrub techs, or others, to interact with the video and phaco system parameters and/or GUI controls without having to refocus on an object between near and far distances. This would better assist the staff during surgery and eliminates the need to focus their eyes on multiple distance targets, such as another monitor for information of relevance to the surgical operation. This allows for rapid assessment of the needs of the case and, if required, the staff can interact with the phaco system within the context of what the surgeon is currently doing in the eye, such as changing parameters. Further, this allows the OR staff to direct more attention to the patient, surgeon and phaco system during surgery. The present invention provides a phacoemulsification surgical system, comprising a surgical console comprising at least one hardware processor and at least one memory, a display, an input device, and a surgical instrument, wherein the display, the input device, and the surgical instrument are communicatively coupled to the surgical console, and wherein at least one image or video captured by a camera communicatively coupled with the surgical console is delivered to the display via the surgical console responsive to the input device.

The present invention provides a method for viewing a surgery, comprising providing, on a display, a live video feed of a surgical procedure and controlling the video feed with an input device, wherein the display and the input device are communicatively coupled with a surgical console, and wherein the video feed comprises only a portion of the display. The method further provides that the video feed consists of at least one attribute selected from the group consisting of size, location, visibility, color, and contrast is controlled responsive to the input device.

BRIEF DESCRIPTION OF THE DRAWINGS

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

The detailed description makes reference to the accompanying figures in which.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

In a first embodiment, a real-time video feed of a patient's eye as part of status information visible to a user/scrub tech throughout surgery is provided. This status video may be available when there is a connection between a surgical microscope and phaco system. This video feed may be visible among other surgical parameters on the screen (including but not limited to: set points for vacuum/power/flow, real-time values of vacuum/power/flow, surgical modes, bottle height, balanced salt solution (BSS) usage, continuous irrigation, effective phaco time (EPT), etc.). These surgical parameters may be accessible at the time the video feed is visible. In the event the video feed is not visible, or accessible, one or more surgical parameters may be accessible or visible on the GUI.

In a second embodiment, a real-time video feed having its own panel among other panels contained on the GUI screen may be provided showing surgical parameters, programs, and other menus, for example. The video feed may, for example, be automatically visible when a camera and/or video feed is detected by the phaco system. This video feed visual may be visible among the other surgical parameters on the screen (including but not limited to: set points for vacuum/power/flow, real-time values of vacuum/power/flow, surgical modes, bottle height, BSS usage, continuous irrigation, EPT, etc.). These surgical parameters may also be accessible at the time the video feed is visible. If a camera/video feed is not detected by the phaco system, the video feed panel may not be accessible/visible.

Figure 1:
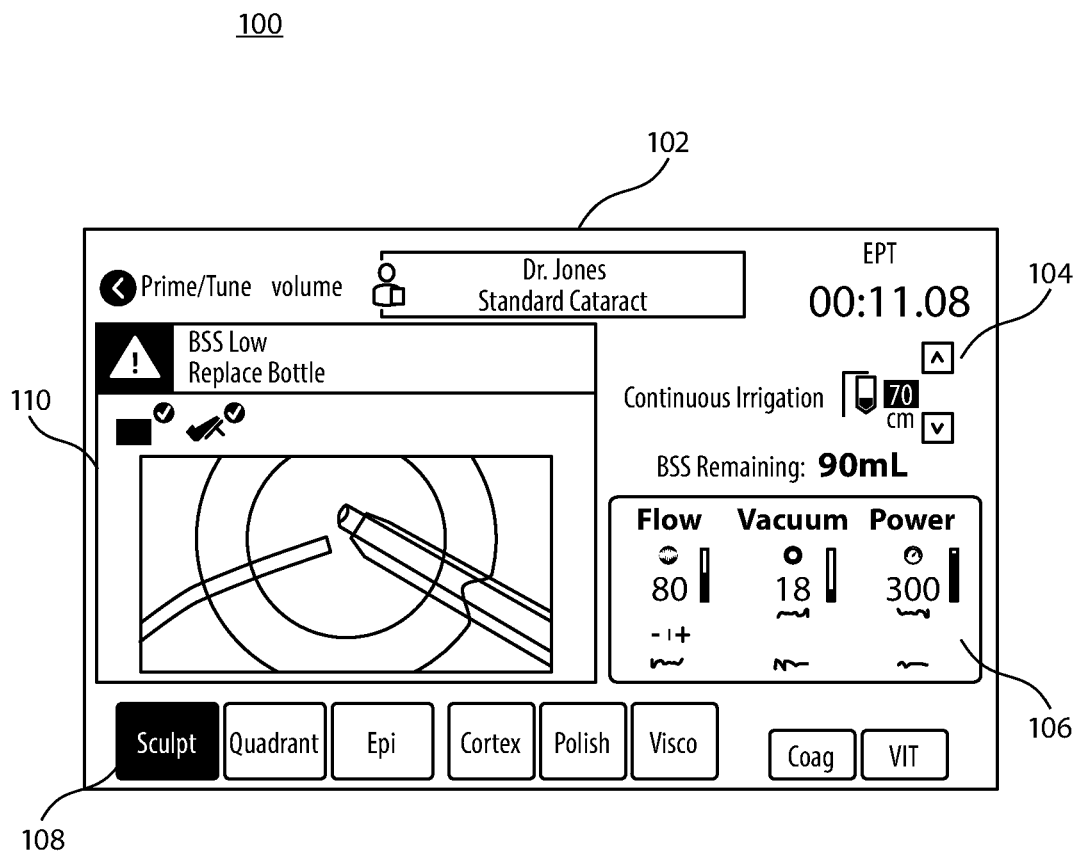
FIG. 1 illustrate a rendition of a graphical user interface in accordance with at least one embodiment of the disclosed invention.
Figure 2B:
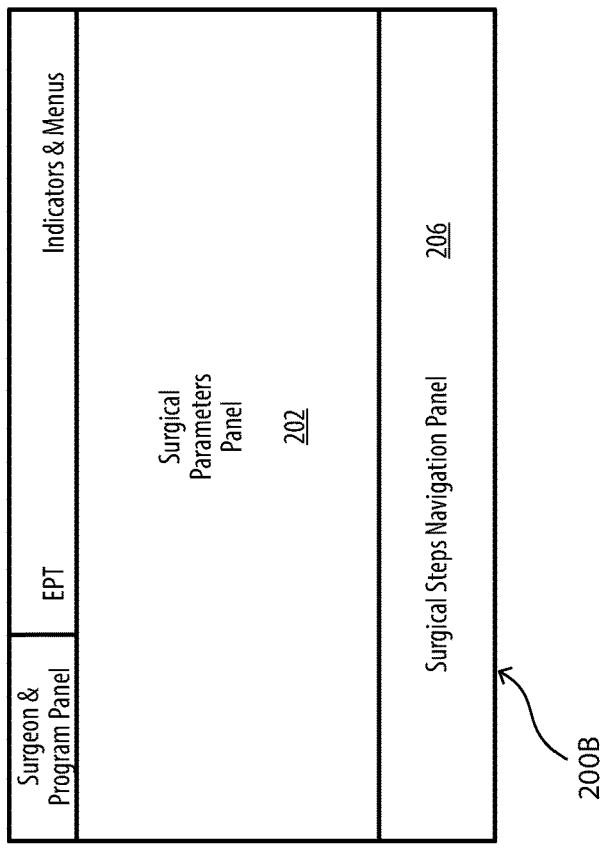
FIGS. 2A and 2B illustrate user interface implementations in accordance with one or more embodiments of the disclosed invention.
Figure 2A:
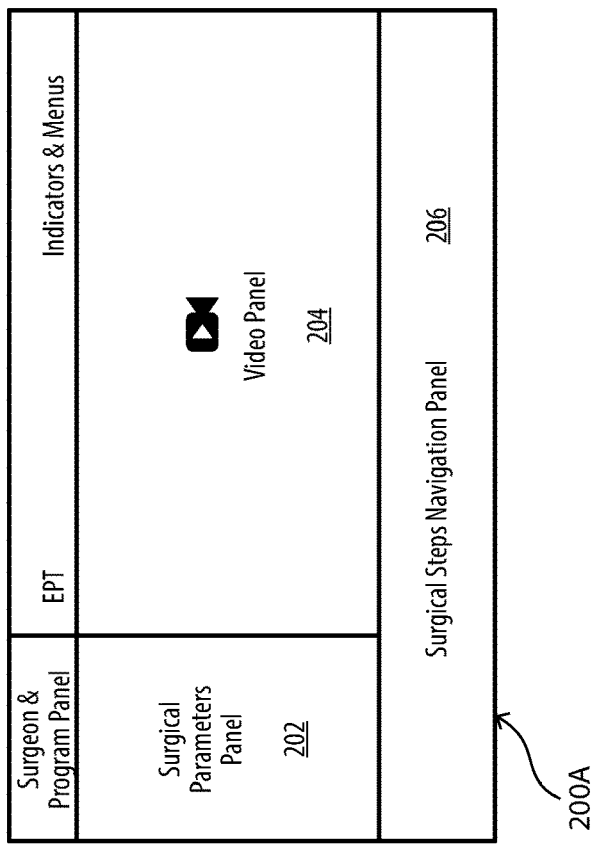

FIG. 1 illustrates a rendition of a graphical user interface (GUI) 100 of an embodiment of the disclosed invention. The GUI is not meant to be limited to any certain orientation, such as portrait or landscape. While the examples of FIGS. 1, 2A, and 2B are shown in landscape orientation, it is to be understood that other orientations may be used. GUI 100 may comprise a plurality of modules providing various information to a viewer of the GUI. Various information may include, but is not limited to, surgeon/surgery information 102 and surgical parameter data 104. For example, IV bottle height, and infusion pressure control. Also shown in the module may be a continuous irrigation button. Further, surgical data 106 data derived from sensors may be shown. For example, flow, vacuum, and power settings may be shown in real-time. Module buttons may be static or responsive. For example, responsive +/− buttons may allow for adjustments to be made to different settings with respect to flow, vacuum, or power settings, for example. Other settings may be adjusted accordingly. Mode Navigation buttons 108 allow for a toggle between different modes, or steps, during cataract surgery. Typical modes, or steps, employed during cataract surgery when using a phacoemulsification handpiece may include, but are not limited to: Sculpt (i.e. phacoemulsification of the cataract into small fragments), Quadrant (i.e. cataract removal mode), or Epi (i.e. epinucleus), Cortex (i.e. removal of residual cortex), Polish (i.e. anterior capsule polishing), and Visco (i.e. viscoelastic-removal) modes. Module 110 is a status region. Box 110 may show the status of the surgical instrument as well as a live video feed of the surgical instrument being used in conjunction with the eye.

The phacoemulsification system may contain two articulable displays. One screen may be positioned in front of a scrub tech and contain either the live video feed, surgical parameters (including but not limited to: set points for vacuum/power/flow, real-time values of vacuum/power/flow, surgical modes, bottle height, BSS usage, continuous irrigation, EPT, etc.), or both. A second screen may be positioned closer to a console body and contain only surgical parameters. A remote device (such as an app on a wireless device) may contain either the live video feed, surgical parameters, or both. Both the remote device and the console may have voice command capability to command when to show the live video feed and specify which device to display it onto. This would allow for flexibility and accommodate users and their unique preferences for ways to access the video feed, whether it be via direct GUI contact or remotely with a remote device by way of voice command.

FIGS. 2A and 2B illustrate diagrams showing exemplary GUI implementations 200A and 200B. A typical GUI implementation may be comprised of one or more individual panels or layers. In FIG. 2A, an exemplary panel, 200A, shows a panel having a video feed panel 204. Other panels may be shown, such as Surgical Parameters Panel 202 and Surgical Steps Navigation Panel 206, among others. In FIG.

2B, an exemplary panel 200B shows a GUI having a panel having no video feed available and merely shows Surgical Parameters Panel 202 and Surgical Steps Navigation Panel 206, among others. A Video Panel, such as Panel 204, may automatically determine when a video feed is available. For example, panel 200A shows that a camera connection is detected and a video feed 204 may be exposed automatically. Alternatively, panel 200B shows that a camera connection is not detected and therefore a video feed, not being available, is concealed. Different panels may temporarily overlap or overlay when certain surgical events are triggered, such as occlusions, pressure spikes, and fluid loss, for example. Further, different panels may permanently overlap or overlay based on inputs received by the GUI, such as certain menu buttons or status indicators activated by a touchscreen of the GUI.

In another embodiment, a video feed of a real-time visual of a patient's eye may be visible on a phaco system GUI depending on a foot pedal activation. When the surgeon applies irrigation, vacuum, and/or power (foot pedal zones 1, 2, and 3, for example), a video feed window may automatically appear to allow a scrub tech, for example, the ability to view the patient's eye on the GUI. The video feed window may expand out over the entire GUI screen or may only expand over a portion of the entire GUI screen. In an embodiment, nothing else on the screen (i.e. the surgical parameters) may be visible as long as the video feed is opened or alternatively, the video feed may be visible as well as one or more surgical parameters. This would allow the scrub tech to follow and be aware of the cataract removal status for all modes. In an embodiment, when the foot pedal is in a position other than 2 and 3 (position 1 for irrigation or not pressed at all, for example), the video feed window would no longer be visible. Instead, the visuals initially on the screen (i.e. surgical parameters including but not limited to: set points for vacuum/power/flow, real-time values of vacuum/power/flow, surgical modes, bottle height, BSS usage, continuous irrigation, EPT, etc.) may now be visible as long as the video feed is not opened. When the foot pedal is in, for example, position 1 or not pressed at all, the user may be able to access other GUI settings and/or troubleshoot as needed without the video feed expanded on the screen. The expansion and close out implementation of the video feed would be a smooth and fade in/out transition so as not to be disruptive to the user.

Alternatively, there may be a dedicated button on the GUI for manually accessing the video feed. Pressing this button may trigger the video feed window to expand out over the entire GUI screen. There may also be an exit button on the top of the video feed window to manually close out the video feed, if desired. There may be an option on the phaco system to turn on/off the feature for automatic video feed window expansion/close out. If the user decides to turn off this feature, when the foot pedal is activated in positions 1, 2, or 3, the video feed window may not automatically expand. A dedicated button on the GUI would allow for manual access to the video feed. The video feed close out would be done manually.

In addition to tying the video feed window expansion/close out with the foot pedal activations, an additional condition may be to tie it to detecting whether the hand piece tip is submerged in the eye (or some fluid). This is for considering the cases when staff is using the hand piece and may be troubleshooting with surgical parameters on the GUI outside of the eye. The video feed window may not be useful in this instance. Combining hand piece submerge detection and foot pedal activation to dictate video feed window expansion/close out would be useful.

Figure 3:
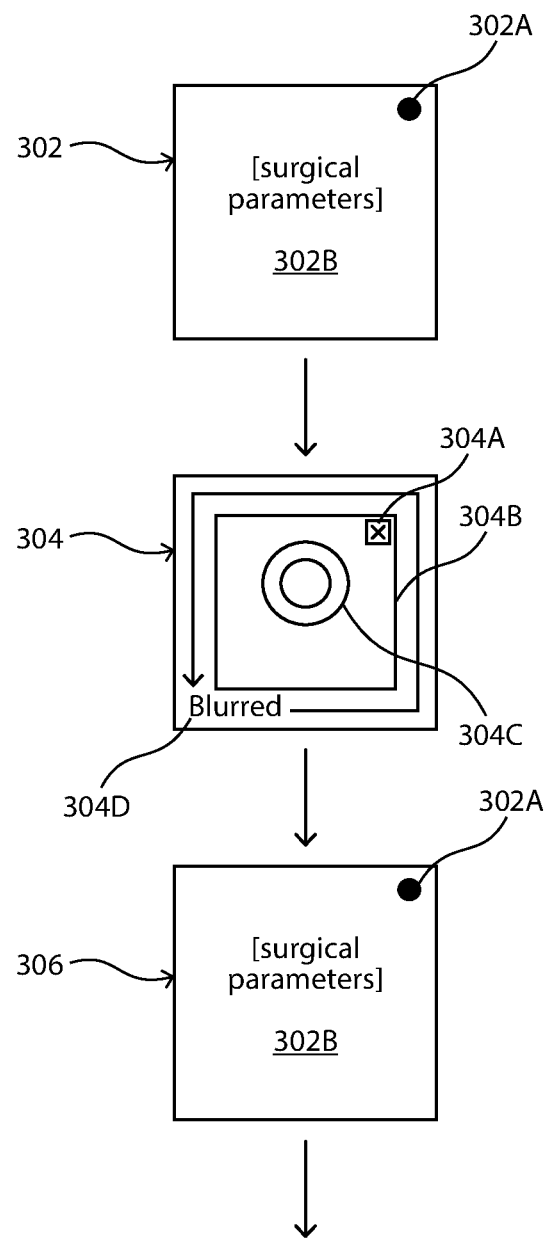
FIG. 3 illustrates a series of user interface implementations based on user actions in accordance with one or more embodiments of the disclosed invention.

FIG. 3 illustrates a flow diagram 300 of a series of user interface implementations based on user actions. A user interaction may be simply the depressing of a foot pedal by a surgeon. Video window pop-ups may occur in response to user actions. In another embodiment, a video pop-up may occur in response to a surgery condition that requires immediate attention, such as a possible detection of handpiece being submerged in water or other liquid. As shown, in step 302, a GUI may be shown on a video display having a view of a surgical screen just prior to the surgical procedure. A dedicated button 302A may be displayed to allow for on-demand access and display of a live video visual window upon input received (i.e. touchscreen controls). Various surgical parameters 302B may be shown within the GUI. Surgical parameters 302B may include, but not limited to, initial set points for power, vacuum, and flow rate. Other surgical statistics may be shown, such as bottle height, EPT (effective phaco time) Timer, etc. Upon receiving input from a user, such as a foot pedal activation, the GUI may progress to the overlay of image 304. Overlay 304 illustrates a real-time live video feed 304B of the surgical operation. Button 304A may be selected by a user to exit the live video feed window. The live video feed 304B may show a live video visual 304C of a patient's eye being operated on. Visual parameters 304D may be shown, albeit blurred. The surgical parameters would be overlaid by video feed window 304B and therefore not entirely visible. The live video feed may be transmitted to the display from a camera that is attached, for example, to a surgical microscope.

In another alternative embodiment, video feed window size may be of differing sizes. For example, the video feed window may be smaller and take a "picture in picture" effect. When expanded, it would not cover the entire GUI screen but instead take about ¼ of the screen. The expansion and close out implementation of the video feed would be a smooth and fade in/out transition so as not to be disruptive to the user. The surgical parameters (including but not limited to: set points for vacuum/power/flow, real-time values of vacuum/power/flow, surgical modes, bottle height, BSS usage, continuous irrigation, EPT, etc.) initially on the screen would get shifted around to fit in the remaining ¾ of the GUI screen.

Figure 4:
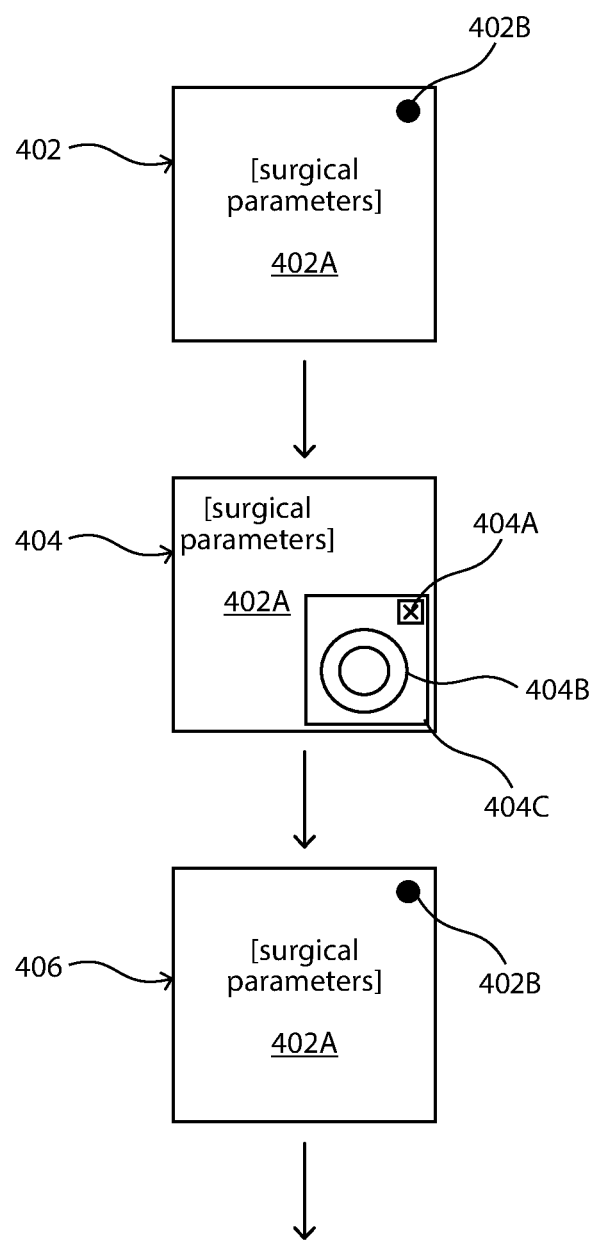
FIG. 4 illustrates a series of user interface implementations based on user actions in accordance with one or more embodiments of the disclosed invention.

FIG. 4 illustrates a series of alternate user interface implementations based on user actions. Flow diagram 400 shows a series of user interface implementations based on user actions. A user interaction may be simply the depressing of a foot pedal by a surgeon. Video window pop-ups may occur in response to user actions. In another embodiment, a video pop-up may occur in response to a surgery condition that requires immediate attention, such as a possible detection of handpiece submerge as described herein and above. As shown, in step 402, a GUI may be shown on a video display having a view of a surgical screen just prior to the surgical procedure with surgical parameters 402A. A dedicated button 402B may be displayed to allow for on-demand access and display of a live video visual window upon input received (i.e. touchscreen controls). Surgical parameters 402A may include, but not limited to, initial set points for power, vacuum, and flow rate. Other surgical statistics may be shown, such as bottle height, EPT Timer, etc. Upon receiving input from a user, such as a foot pedal activation, the GUI may progress to the overlay of image 404. Overlay 404 illustrates a real-time live video feed 404B of the surgical operation as a picture-in-picture implementation as described above. Button 404A may be selected by a user to exit the live video feed window. The live video feed 404C may show a live video visual 404B of a patient's eye being operated on. Visual parameters 402A may be shown in conjunction with the video feed 404C. The live video feed may be transmitted to the display from a camera that is attached, for example, to a surgical microscope. In response pedal activation or touchscreen input, the process would move to overlay 406 showing surgical parameters 402A and button 402B.

In yet another embodiment, manual access of the video feed window per a dedicated button on the GUI screen may be provided. For this first rendition, pressing a button would trigger the video feed window to expand out over an entire GUI screen. There may be an exit button on the top of the video feed window to manually close out the video feed, if desired. The video feed may expand out to take over the entire GUI screen.

In this embodiment, the video feed expanding out may take up about one quarter of the screen. Alternatively, the video feed may fill less than one quarter of the screen or more than one quarter of the screen. The surgical parameters (including but not limited to: set points for vacuum/power/flow, real-time values of vacuum/power/flow, surgical modes, bottle height, BSS usage, continuous irrigation, EPT time, etc.) initially on the screen may get shifted around to fit in the remaining three quarters of the GUI screen.

Figure 5:
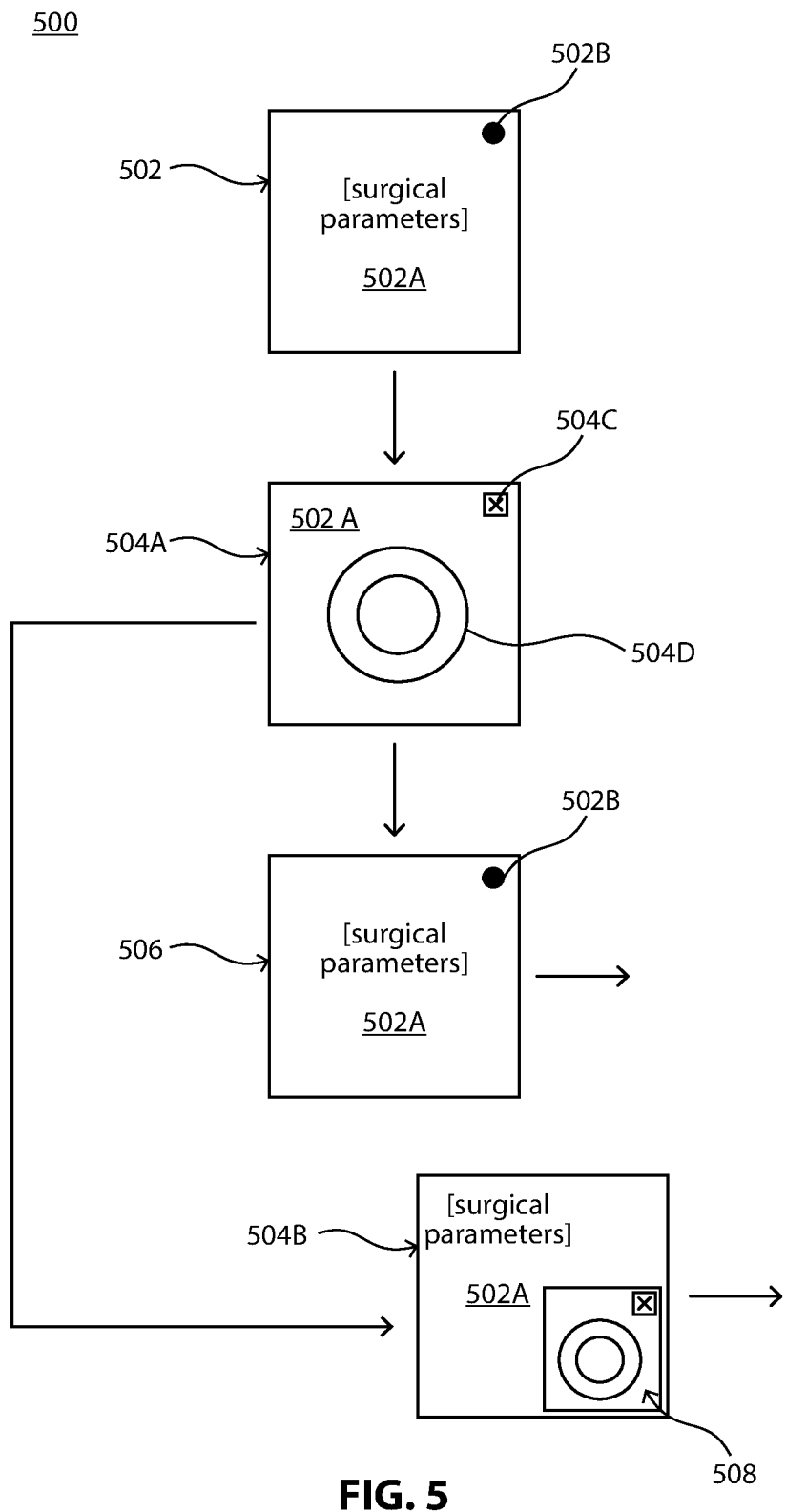
FIG. 5 illustrates on-demand video feed implementations in accordance with one or more embodiments of the disclosed invention.

FIG. 5 illustrates an on-demand video feed implementation having a series of alternate user interface implementations based on user actions. Flow diagram 500 shows a series of user interface implementations based on user actions. A user interaction may be input received via a touchscreen display or may also be input received by depressing the foot pedal or selection of a button on the foot pedal. Video window pop-ups may occur in response to user actions. As shown, in step 502, a GUI may be shown on a video display having a view of a surgical screen just prior to the surgical procedure with surgical parameters 502A. A dedicated button 502B may be displayed to allow for on-demand access and display of a live video visual window upon input received (i.e. touchscreen controls). Surgical parameters 502A may include, but not limited to, initial set points for power, vacuum, and flow rate. Other surgical statistics may be shown, such as bottle height, EPT Timer, etc. Upon receiving input from a user, such as a foot pedal activation, the GUI may progress to the overlay of image 504A. Overlay 504A illustrates a real-time live video feed 504D of the surgical operation as a picture-in-picture implementation as described above. Button 504C may be selected by a user to exit the live video feed window. The live video feed 504D may show a live video visual of a patient's eye being operated on. The live video feed may be transmitted to the display from a camera that is attached, for example, to a surgical microscope. In response to a user input, e.g. to touchscreen input, the process would move to overlay 506 or overlay 504B, based on user settings. For example, overlay 506 hides the entire video feed entirely and merely shows surgical parameters 502A and dedicated button 502B, as described above. Overlay 504B may show the video feed panel as a picture-in-picture implementation 508 alongside surgical parameters 502A.

In yet another embodiment of the disclosed invention, the video feed may be a dominating visual on a phaco system GUI with one or more surgical parameters (including but not limited to: set points for vacuum/power/flow, real-time values of vacuum/power/flow, surgical modes, bottle height, BSS usage, continuous irrigation, EPT time, etc.) still visible although they will be faded out to allow for the video to be the dominating visual on the GUI. This view may be the main view and only allow for changing the surgical modes (i.e. navigating from sculpt to chop to quadrant) via remote control device and/or directly pressing on the GUI.

Figure 6:
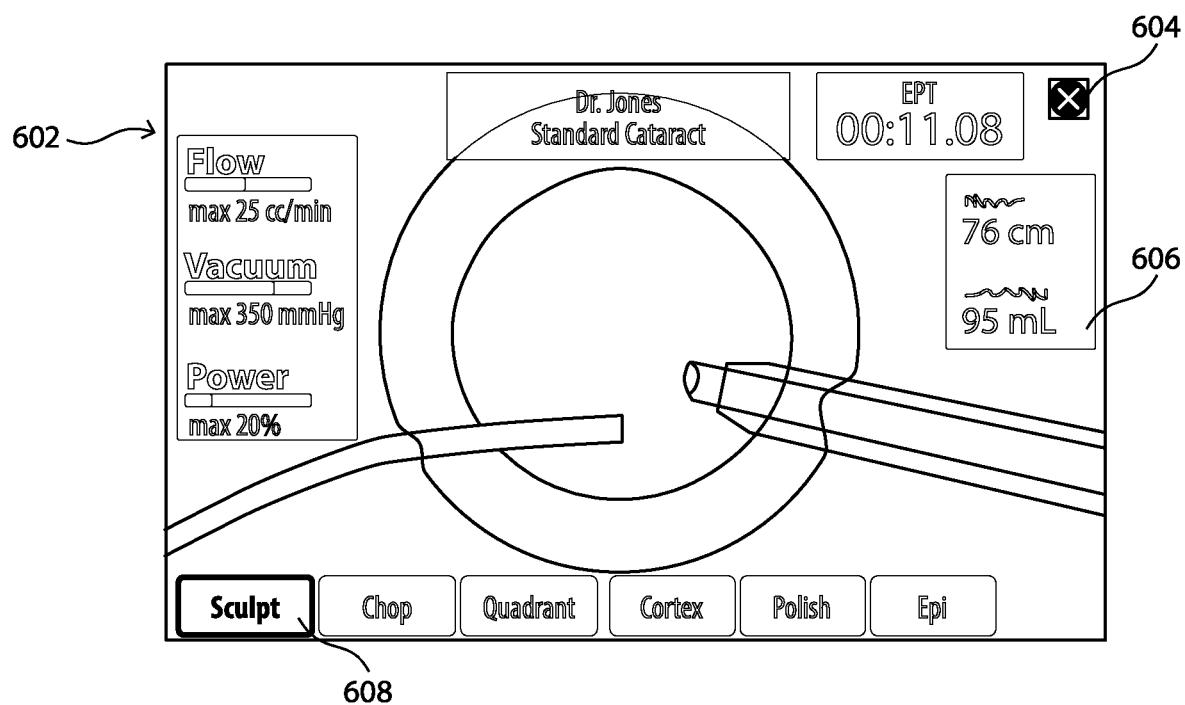
FIG. 6 illustrates an exemplary video display having live video with overlay (no control) in accordance with at least one embodiment of the disclosed invention.

FIG. 6 illustrates an exemplary video display 600 having live video with overlay (no control). GUI 602 may show a live video feed of the surgical operation, as described herein and above. Different modules, or panels, may show the surgeon and surgery being performed, an exit button "X" 604, current surgical parameters 606 being measured by one or more sensors, a menu panel 608, and certain settings (such as Flow, Vacuum, and Power). Surgical information, such as parameters 606 and menu panel 608, may be shown, however, this information may be shown as a slightly faded overlay, for example. In this example, the live video feed would be the dominant view. Further, a recording component may be included for recording the live feed of a surgery, such as a cataract surgery described herein. The recorded video feed may be stored for later retrieval, such as on a memory or the like. Recording of the video feed enables the playback of the live video feed for subsequent review by one or more surgeons, for example.

Figure 7:
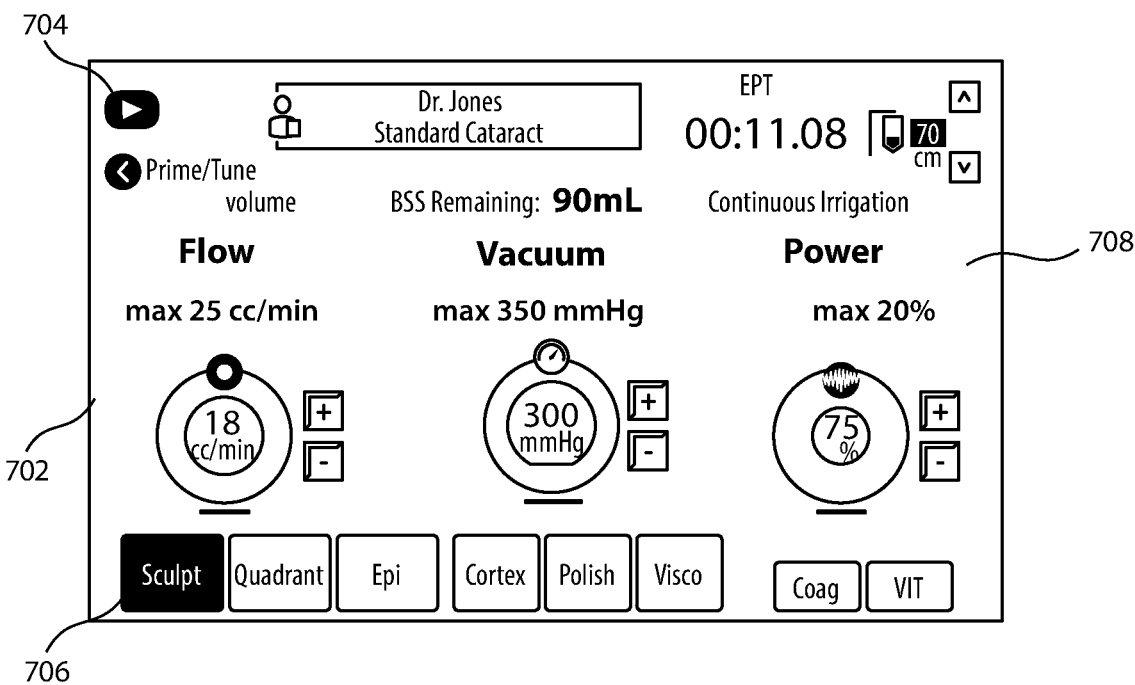
FIG. 7 illustrates an exemplary graphical user interface having a surgical control view with no live video feed in accordance with at least one embodiment of the disclosed invention.

A user may press X 604 at the top right by a remote control device and/or directly pressing on the GUI (via touchscreen control) to navigate from the main view to the surgical control screen 700 of FIG. 7. The screen of FIG. 7 allows access to and change the various settings including but not limited to: set points for vacuum/power/flow, real-time values of vacuum/power/flow, surgical modes, bottle height, BSS usage, continuous irrigation, EPT time. If a camera/video feed is not detected by the phaco system, the screen would default to the image of overlay 702. The red play live video button 704 in the upper left corner would then be faded out and not accessible. Separate panels or modules may be made available. For example, certain settings may be adjusted by a user via settings panel 708. Exemplary settings include, but are not limited to, Flow, Vacuum, and Power. Mode panel 706 may be provided to allow a user to quickly switch between different operating modes of the phaco console.

Figure 8:
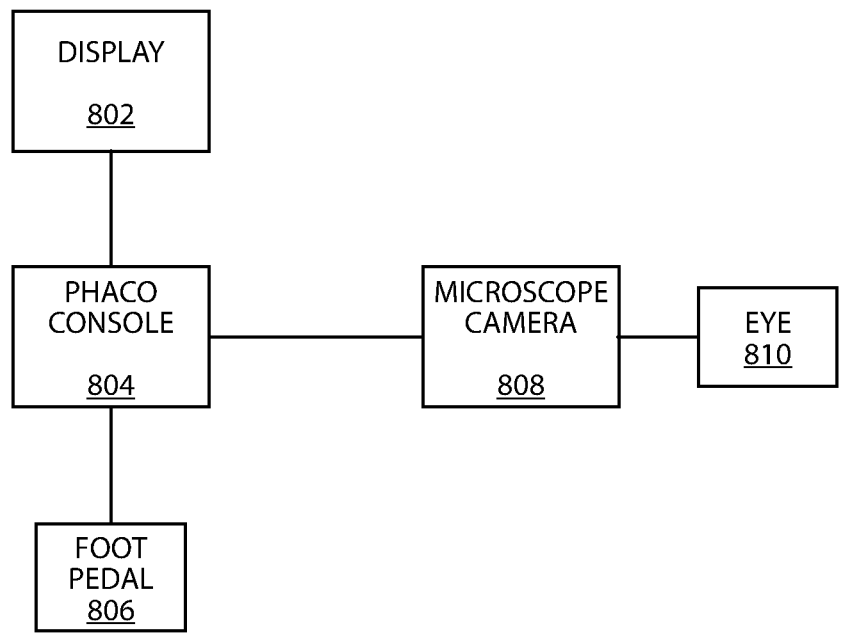
FIG. 8 illustrates a diagram of an exemplary computing environment in accordance with one or more embodiments of the disclosed invention.
Figure 9:
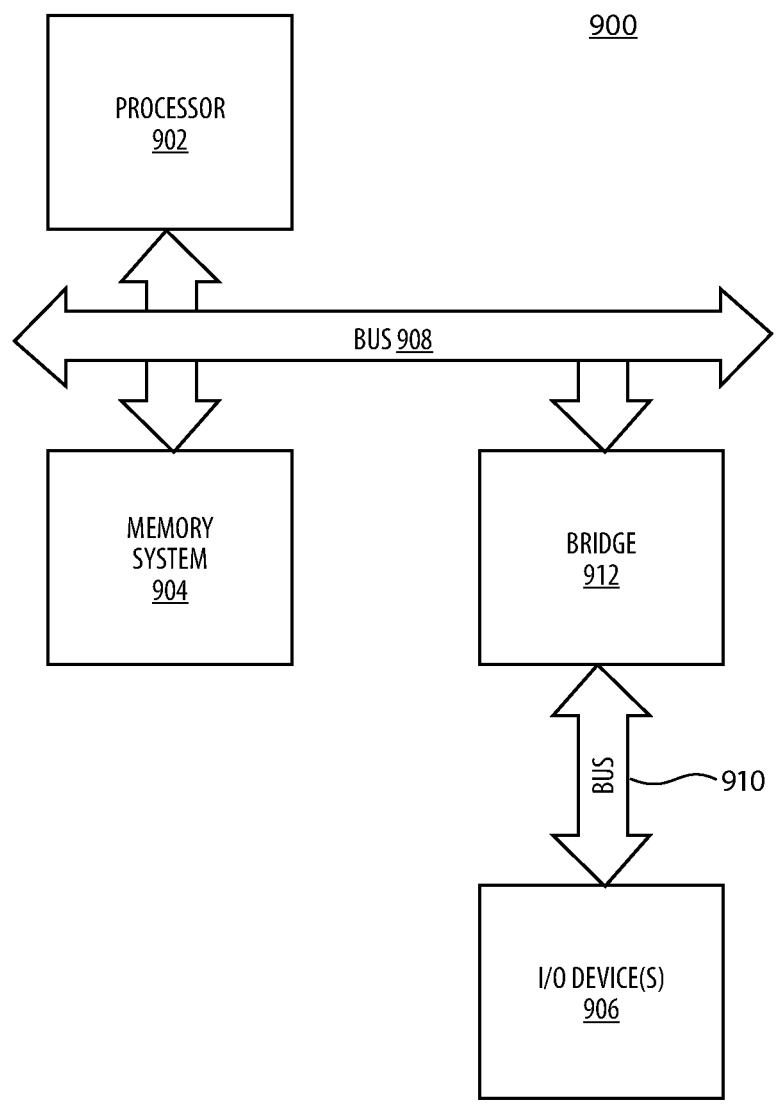
FIG. 9 illustrates a diagram of an exemplary computing system in accordance with one or more embodiments of the disclosed invention.

As illustrated in FIG. 8, embodiments of the phacoemulsification system may include various components, hardware elements, software elements, and combinations thereof. FIG. 8 illustrates an exemplary computing environment 800 of the disclosed invention. Display 802 may be a computer screen, a television monitor, a mobile device screen or the like. Display may be communicatively coupled either wired or wirelessly to a phacoemulsification console 804. In communication with the phaco console may be a foot pedal 806, as described herein and above. A microscope camera 808 may be communicatively coupled to the phaco console 804, either wired or wirelessly. Camera 808 may be attached to either a surgeon or a surgical handpiece (not shown) which provides live video feed of the surgical procedure, such as of eye 810. It is understood that the described arrangement is exemplary and may be modified without departing from the spirit or scope of the invention FIG. 9 is an example of a simplified functional block diagram of a computer system 900. The functional descriptions of the present invention can be implemented in hardware, software or some combination thereof.

As shown in FIG. 9, the computer system 900 includes a processor 902, a memory system 904 and one or more input/output (I/O) devices 906 in communication by a communication 'fabric'. The communication fabric can be implemented in a variety of ways and may include one or more computer buses 908, 910 and/or bridge and/or router devices 912 as shown in FIG. 9. The I/O devices 906 can include network adapters and/or mass storage devices from which the computer system 900 can send and receive data for generating and transmitting advertisements with endorsements and associated news. The computer system 900 may be in communication with the Internet via the I/O devices 908.

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

The various illustrative logics, logical blocks, modules, and engines, described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of instructions on a machine readable medium and/or computer readable medium.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

The invention claimed is:

1. A phacoemulsification surgical system, comprising:
   a surgical console comprising at least one hardware processor and at least one memory;
   a display;
   an input device; and
   a surgical instrument;
   wherein the display, the input device, and the surgical instrument are communicatively coupled to the surgical console; and
   wherein at least one real-time image or real-time video captured by a camera communicatively coupled with the surgical console is delivered to the display via the surgical console in response to a condition of the surgical instrument, the condition including at least whether the surgical instrument is submerged in a fluid.

2. The surgical system of claim 1, wherein the display comprises a graphical user interface comprising a plurality of panels.

3. The surgical system of claim 2, wherein at least one of the plurality of panels comprises a video feed panel.

4. The surgical system of claim 3, wherein the video feed panel shows a video feed in response to a video feed being detected by the surgical system and the video feed panel is hidden in response to no video feed being detected by the surgical system.

5. The surgical system of claim 3, wherein the video feed panel is hidden in response to no video feed being detected by the surgical system.

6. The surgical system of claim 3, wherein the video feed panel is overlaid on the plurality of panels as a picture-in-picture panel.

7. The surgical system of claim 6, wherein the video feed panel takes up about one quarter of the available display space.

8. The surgical system of claim 2, wherein at least one of the plurality of panels displays surgical parameters.

9. The surgical system of claim 8, wherein the surgical parameters comprise one or more of: set points for vacuum/power/flow, real-time values of vacuum/power/flow, surgical modes, bottle height, balanced salt solution (BSS) usage, continuous irrigation, and effective phaco time (EPT).

10. The surgical system of claim 1, wherein the display comprises a touchscreen device.

11. The surgical system of claim 1, wherein the input device comprises a foot pedal.

12. The surgical system of claim 1, wherein the surgical instrument comprises a phacoemulsification handpiece.

13. The surgical system of claim 1, wherein the camera is attached to a surgical microscope.

14. The surgical system of claim 1, wherein at least one attribute of the at least one image or video selected from the group consisting of size, location, visibility, color, and contrast is controlled responsive to the input device.

15. The surgical system of claim 1, wherein the at least one image or video captured by the camera is recorded onto a memory for subsequent retrieval.

16. A method for viewing a surgery, comprising:
providing, on an electronic display, a live video feed of a surgical procedure; and
controlling the video feed with an input device;
wherein the display and the input device are communicatively coupled with a surgical console comprising a surgical instrument,
wherein the video feed comprises only a portion of the display, and
displaying the video feed on at least a portion of the display in response to a condition of the surgical instrument, the condition including at least whether the surgical instrument is submerged in a fluid.

17. The method of claim 16, wherein the video feed consists of at least one attribute selected from the group consisting of size, location, visibility, color, and contrast is controlled responsive to the input device.

18. The method of claim 17, wherein the controlling at least one attribute of the video feed with an input device is limited to predetermined display parameters.

19. The method of claim 16, wherein the input device comprises a footpedal.

20. The method of claim 16, wherein the video feed is provided by at least one camera in communication with the surgical console.

21. The method of claim 16, wherein the video feed is overlaid as a picture-in-picture panel on the display.

22. The method of claim 16, wherein the video feed takes up about one quarter of the available display space.

23. The method of claim 16, wherein the display comprises information related to surgical parameters selected from the group consisting of vacuum flow, power, surgical mode, bottle height, balanced salt solution (BSS) usage, irrigation pressure, and effective phaco time (EPT).

24. The method of claim 16, wherein the display is a touchscreen device.

25. The method of claim 16, wherein the surgical console is in communication with a phacoemulsification handpiece.

26. The method of claim 16, further comprising:
recording the video feed; and
storing the recorded feed for subsequent retrieval.

* * * * *